(12) United States Patent
Sly et al.

(10) Patent No.: US 8,784,833 B2
(45) Date of Patent: Jul. 22, 2014

(54) PRENATAL ENZYME REPLACEMENT THERAPY FOR HYPOPHOSPHATASIA

(75) Inventors: William S. Sly, St. Louis, MO (US); Jeffrey H. Grubb, Arnold, MO (US); Shunjl Tomatsu, Clayton, MO (US); Adriana Maria Montaño Suarez, St. Louis, MO (US); Hirotaka Oikawa, Singapore (SG)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 13/007,772

(22) Filed: Jan. 17, 2011

(65) Prior Publication Data

US 2011/0300143 A1 Dec. 8, 2011

Related U.S. Application Data

(63) Continuation-in-part of application No. 11/769,693, filed on Jun. 27, 2007, now Pat. No. 7,871,624.

(60) Provisional application No. 60/805,954, filed on Jun. 27, 2006.

(51) Int. Cl.
*A61K 39/00* (2006.01)
*C07K 19/00* (2006.01)
*C12N 9/14* (2006.01)
*A61K 38/43* (2006.01)

(52) U.S. Cl.
CPC . *C07K 19/00* (2013.01); *C12N 9/14* (2013.01); *C07K 2319/00* (2013.01); *C07K 2319/003* (2013.01); *C07K 2319/30* (2013.01); *A61K 38/43* (2013.01); *Y10S 424/809* (2013.01); *Y10S 530/866* (2013.01)
USPC .............. 424/192.1; 424/134.1; 424/809; 530/350; 530/866

(58) Field of Classification Search
None
See application file for complete search history.

(56) References Cited

U.S. PATENT DOCUMENTS

| | | | | |
|---|---|---|---|---|
| 5,580,859 | A * | 12/1996 | Felgner et al. | 514/44 R |
| 5,929,304 | A | 7/1999 | Radin et al. | |
| 6,359,054 | B1 * | 3/2002 | Lemieux et al. | 524/505 |
| 6,475,486 | B1 | 11/2002 | Kolar et al. | |
| 7,871,624 | B2 * | 1/2011 | Grubb et al. | 424/185.1 |
| 7,943,126 | B2 * | 5/2011 | Tomatsu et al. | 424/94.1 |
| 2004/0005309 | A1 * | 1/2004 | LeBowitz et al. | 424/94.61 |
| 2005/0142140 | A1 * | 6/2005 | Massberg et al. | 424/178.1 |
| 2007/0081984 | A1 * | 4/2007 | Tomatsu et al. | 424/94.6 |
| 2008/0025995 | A1 * | 1/2008 | Grubb et al. | 424/178.1 |
| 2010/0297119 | A1 * | 11/2010 | Crine et al. | 424/134.1 |
| 2011/0300143 | A1 | 12/2011 | Sly et al. | |

FOREIGN PATENT DOCUMENTS

WO 01/36603 A2 5/2001

OTHER PUBLICATIONS

Brady, R. O., "Enzyme Replacement for Lysosomal Disease," Annu. Rev. Med., 57: 283-296, 2006.
Neufeld, E. F., et al (2001) The Metabolic and Molecular Bases of Inherited Disease, eds. Scriver, C. R., Beaudet, A. L., Sly, W. S., & Valle, D. (McGraw-Hill, New York), vol. III, 8th edition, pp. 3421-3451.
Nelson, et al. Mucopolysaccharisosis VII presenting as nonimmune hydrops fetalis, (Oct. 1982) Journal of Pediatrics, 101:574.
Gheti, et al., Multiple Roles for the Major Histocompatibility Complex Class I-Related Receptor FcRn. Annu. Rev. Immunol. (2000) 18:739-766.
Niwa, et al., Efficient selection for high-expression transfectants with a novel eukaryotic vector. Gene 108, (1991) 193-200.
Ulmasov, et al., Purification and kinetic analysis of recombinant CAXII, a membrane carbonic anhydrase overexpressed in certain cancers. PNAS (2000), vol. 97 No. 26 14212-14217.
Islam, et al., C-terminal Processing of Human β-glucuronidase. (1993) Journal of Biological Chemistry vol. 268 (30):22627-22633.
Von Figura, et al., Lysosomal enzymes and their receptors. (1986)., Annu. Rev. Biochem. 55: 167-193.
Hickman, et al., A recognition marker required for uptake of a lysosomal enzyme by cultured fibroblasts. 1974, Biochemical and Biophysical Research Communications vol. 57, Issue 1, 55-61.
Orii, et al., Defining the pathway for Tat-mediated delivery of beta-glucuronidase in cultured cells and MPS VII mice, (2005) Molecular Therapy vol. 12, 2, 345-352.
Nishioka et al, Enhancement of drug delivery to bone: Charactereization of human tissue-nonspecific alkaline phosphatase tagged with an acidic oligopeptide, Molecular Genetics and Metabolism, 2006, 88(3):244-255.
Millan et al, Enzyme Replacement Therapy for Murine Hypophosphatasia, (2008) Journal of Bone and Mineral Research, vol. 23(6):777-787.
Whyte et al., Hypophosphatasia: Treatment of Life-Threatening Disease Using Bone-Targeted Human Recombinant Tissue Non-Specific Alkaline Phosphatase (2009) ACR/ARHP Scientific Meeting, found at http://acr.confex.com/acr/2009/webprogram/Paper12463.html.

(Continued)

*Primary Examiner* — Michael Szperka
(74) *Attorney, Agent, or Firm* — Mark E. Stallion, Esq.; Husch Blackwell LLP (57) ABSTRACT

Transplacental enzyme replacement therapy (ERT) is disclosed for deficiency of a polypeptide such as a tissue-nonspecific alkaline phosphatase (TNSALP) by administering a pharmaceutical composition that comprises a water-soluble TNSALP portion, e.g., C-terminus-truncated TNSALP peptide-bonded to an IgG1 antibody Fc portion, to a pregnant animal whose fetus or embryo is in need of such therapy. Also contemplated is a method for treating a metabolic disorder, such as HPP, in a fetus or embryo where a fusion protein that comprises a Fc fragment of an IgG1 antibody peptide-bonded to TNSALP is administered to a pregnant mother. The protein crosses the placenta of the mother and enters the fetal blood stream. The protein is taken up into fetal tissue such that the TNSALP restores normal metabolic activity in the fetus.

2 Claims, 4 Drawing Sheets

(56) References Cited

OTHER PUBLICATIONS

Grubb, et al., Infused Fc-tagged β-glucoronidase crosses the placenta and produces clearance of storage in utero in mucopolysaccharidosis VII mice, PNAS, Jun. 17, 2008, vol. 105, No. 24.

Ashkenazi, et al., Immunoadhesins as research tools and therapeutic agents, Curr Opin Immunol. Apr. 1997; 9:195-200.

Becker, et al., Kinetic Data of in-vivo labeled granulocytes in humans with a murine Tc-99m-labelled monoclonal antibody, Eur J Nucl Med, 1989, 15:361-366, abstract only.

Lebowitz, et al., Glycosylation-independent targeting enhances enzyme delivery to lysosomes and decreases storage in mucopolysaccharidosis type VII mice, PNAS, Mar. 2, 2004, vol. 101, No. 9, 3083-3088.

Chinese Hamster Ovary Cell Line American Type Culture Collection, ATCC CRL 9618, printed Jun. 19, 2012 from world wide web. atcc. org.

Laemmli, Cleavage of Structural Proteins during the Assembly of the Head of Bacteriophage T4, (1970) Nature (London) 227, 680-685.

Glaser, et al., Beta-glucuronidase deficiency mucopolysaccharidosis: methods for enzymatic diagnosis. (1973) Journal Lab. Clin. Med. 82: 969-977.

\* cited by examiner

```
                               SEQUENCE LISTING

<160> NUMBER OF SEQ ID NOS: 2

<210> SEQ ID NO 1
<211> LENGTH: 1587
<212> TYPE: DNA
<213> ORGANISM: Artificial
<220> FEATURE:
<223> OTHER INFORMATION: synthetic sequence

<400> SEQUENCE: 1
ccacgtcgat tgcatctctg ggctccaggg ataaagcagg tcttggggtg caccatgatt      60
tcaccattct tagtactggc cattggcacc tgccttacta actccttagt gccagagaaa     120
gagaaagacc ccaagtactg gcgagaccaa gcgcaagaga cactgaaata tgccctggag     180
cttcagaagc tcaacaccaa cgtggctaag aatgtcatca tgttcctggg agatgggatg     240
ggtgtctcca cagtgacggc tgcccgcatc ctcaagggtc agctccacca caaccctggg     300
gaggagacca ggctggagat ggacaagttc cccttcgtgg ccctctccaa gacgtacaac     360
accaatgccc aggtccctga cagcgccggc accgccaccg cctacctgtg tgggtgaag     420 gccaatgagg gcaccgtggg ggtaagcgca gccactgagc gttcccggtg caacaccacc     480
caggggaacg aggtcacctc catcctgcgc tgggccaagg acgctgggaa atctgtgggc     540
attgtgacca ccacgagagt gaaccatgcc acccccagcg ccgcctacgc ccactcggct     600
gaccgggact ggtactcaga caacgagatg cccccctgagg ccttgagcca gggctgtaag     660
gacatcgcct accagctcat gcataacatc agggacattg acgtgatcat gggggggtggc     720 cggaaataca tgtaccccaa gaataaaact gatgtggagt atgagagtga cgagaaagcc     780
aggggcacga ggctggacgg cctggacctc gttgacacct ggaagagctt caaaccgaga     840
tacaagcact cccacttcat ctggaaccgc acggaactcc tgacccttga cccccacaat     900
gtggactacc tattgggtct cttcgagcca ggggacatgc agtacgagct gaacaggaac     960
aacgtgacgg acccgtcact ctccgagatg gtggtggtgg ccatccagat cctgcgcaag    1020
aaccccaaag gcttcttctt gctggtggaa ggaggcagaa ttgaccacgg gcaccatgaa    1080
ggaaaagcca agcaggccct gcatgaggcg gtggagatgg accgggccat cgggcaggca    1140
ggcagcttga cctcctcgga agacactctg accgtggtca ctgcggacca ttcccacgtc    1200
ttcacatttg gtggatacac cccccgtggc aactctatct ttggtctggc ccccatgctg    1260
agtgacacag acaagaagcc cttcactgcc atcctgtatg gcaatgggcc tggctacaag    1320
gtggtgggcg gtgaacgaga gaatgtctcc atggtggact atgctcacaa caactaccag    1380
gcgcagtctc ctgtgcccct gcgccacgag acccacggcg gggaggacgt ggccgtcttc    1440
```

```
tccaagggcc ccatggcgca cctgctgcac ggcgtccacg agcagaacta cgtcccccac    1500
gtgatggcgt atgcagcctg catcggggcc aacctcggcc actgtgctcc tgccagctcg    1560
gcaggcagca ccggtgaagc agaagcc                                        1587
```

<210> SEQ ID NO 2
<211> LENGTH: 529
<212> TYPE: PRT
<213> ORGANISM: Artificial
<220> FEATURE:
<223> OTHER INFORMATION: synthetic sequence

<400> SEQUENCE: 2

```
Pro Arg Arg Leu His Leu Trp Ala Pro Gly Ile Lys Gln Val Leu Gly
1               5                   10                  15

Cys Thr Met Ile Ser Pro Phe Leu Val Leu Ala Ile Gly Thr Cys Leu
            20                  25                  30

Thr Asn Ser Leu Val Pro Glu Lys Glu Lys Asp Pro Lys Tyr Trp Arg
        35                  40                  45

Asp Gln Ala Gln Glu Thr Leu Lys Tyr Ala Leu Glu Leu Gln Lys Leu
    50                  55                  60

Asn Thr Asn Val Ala Lys Asn Val Ile Met Phe Leu Gly Asp Gly Met
65                  70                  75                  80

Gly Val Ser Thr Val Thr Ala Ala Arg Ile Leu Lys Gly Gln Leu His
                85                  90                  95

His Asn Pro Gly Glu Glu Thr Arg Leu Glu Met Asp Lys Phe Pro Phe
            100                 105                 110

Val Ala Leu Ser Lys Thr Tyr Asn Thr Asn Ala Gln Val Pro Asp Ser
        115                 120                 125

Ala Gly Thr Ala Thr Ala Tyr Leu Cys Gly Val Lys Ala Asn Glu Gly
    130                 135                 140

Thr Val Gly Val Ser Ala Ala Thr Glu Arg Ser Arg Cys Asn Thr Thr
145                 150                 155                 160

Gln Gly Asn Glu Val Thr Ser Ile Leu Arg Trp Ala Lys Asp Ala Gly
                165                 170                 175

Lys Ser Val Gly Ile Val Thr Thr Thr Arg Val Asn His Ala Thr Pro
            180                 185                 190

Ser Ala Ala Tyr Ala His Ser Ala Asp Arg Asp Trp Tyr Ser Asp Asn
        195                 200                 205

Glu Met Pro Pro Glu Ala Leu Ser Gln Gly Cys Lys Asp Ile Ala Tyr
    210                 215                 220

Gln Leu Met His Asn Ile Arg Asp Ile Asp Val Ile Met Gly Gly Gly
225                 230                 235                 240

Arg Lys Tyr Met Tyr Pro Lys Asn Lys Thr Asp Val Glu Tyr Glu Ser
                245                 250                 255

Asp Glu Lys Ala Arg Gly Thr Arg Leu Asp Gly Leu Asp Leu Val Asp
            260                 265                 270

Thr Trp Lys Ser Phe Lys Pro Arg Tyr Lys His Ser His Phe Ile Trp
        275                 280                 285

Asn Arg Thr Glu Leu Leu Thr Leu Asp Pro His Asn Val Asp Tyr Leu
    290                 295                 300

Leu Gly Leu Phe Glu Pro Gly Asp Met Gln Tyr Glu Leu Asn Arg Asn
305                 310                 315                 320

Asn Val Thr Asp Pro Ser Leu Ser Glu Met Val Val Val Ala Ile Gln
                325                 330                 335
```

```
Ile Leu Arg Lys Asn Pro Lys Gly Phe Phe Leu Leu Val Glu Gly Gly
            340             345                 350

Arg Ile Asp His Gly His His Glu Gly Lys Ala Lys Gln Ala Leu His
        355             360             365

Glu Ala Val Glu Met Asp Arg Ala Ile Gly Gln Ala Gly Ser Leu Thr
        370             375             380

Ser Ser Glu Asp Thr Leu Thr Val Val Thr Ala Asp His Ser His Val
385             390             395                 400

Phe Thr Phe Gly Gly Tyr Thr Pro Arg Gly Asn Ser Ile Phe Gly Leu
            405             410             415

Ala Pro Met Leu Ser Asp Thr Asp Lys Lys Pro Phe Thr Ala Ile Leu
            420             425             430

Tyr Gly Asn Gly Pro Gly Tyr Lys Val Val Gly Gly Glu Arg Glu Asn
        435             440             445

Val Ser Met Val Asp Tyr Ala His Asn Asn Tyr Gln Ala Gln Ser Pro
450             455             460

Val Pro Leu Arg His Glu Thr His Gly Gly Glu Asp Val Ala Val Phe
465             470             475             480

Ser Lys Gly Pro Met Ala His Leu Leu His Gly Val His Glu Gln Asn
            485             490             495

Tyr Val Pro His Val Met Ala Tyr Ala Ala Cys Ile Gly Ala Asn Leu
            500             505             510

Gly His Cys Ala Pro Ala Ser Ser Ala Gly Ser Thr Gly Glu Ala Glu
            515             520             525

Ala
```

PRENATAL ENZYME REPLACEMENT THERAPY FOR HYPOPHOSPHATASIA

CROSS-REFERENCE TO RELATED APPLICATIONS

This application for patent is a continuation-in-part and claims priority to U.S. patent application Ser. No. 11/769,693, recently allowed, which was filed on Jun. 27, 2007 and claims priority to U.S. Provisional Patent Application No. 60/805,954, which was filed on Jun. 27, 2006. Both disclosures are incorporated by reference.

REFERENCE TO SEQUENCE LISTING

This application contains a Sequence Listing in paper and computer readable form which are the same and are hereby incorporated by reference in their entirety. The nucleic and amino acid sequences listed in the Sequence Listing are shown using standard letter abbreviations for nucleotide bases, and three letter code for amino acids. Only one strand of each nucleic acid sequence is shown, but the complementary strand is understood as included by any reference to the displayed strand.

BACKGROUND OF THE INVENTION

Recent advances in the medical arts have enabled enzyme replacement therapies (ERTs) for a number of metabolic diseases. Those diseases include Gaucher, Krabbe, Fabry and Pompe diseases, as well as various mucopolysaccharidoses (MPS) and hypophosphatasia (HPP).

HPP is an inherited metabolic disorder that features rickets or osteomalacia caused by deficiency of tissue-nonspecific alkaline phosphatase (TNSALP; EC 3.1.3.1). TNSALP is an ubiquitous, cytosol-insoluble plasma membrane-bound enzyme. The human enzyme contains 524 amino acid residues, and the sequence is available on the UniProtKB/Swiss-Prot data base under the designation "PPBT-Human P05186".

Hypophosphatasia is an inherited metabolic disorder of defective bone mineralization caused by deficiency of the TNSALP. Clinical severity is remarkably variable, ranging from death in utero to merely premature loss of dentition in adult life. Despite the presence of TNSALP in bone, kidney, liver, and adrenal tissue in healthy individuals, clinical manifestations in patients with hypophosphatasia are limited to defective skeletal mineralization that manifests as rickets in infants and children and osteomalacia in adults.

In the most pernicious form of hypophosphatasia, the perinatal lethal variant, profound skeletal hypomineralization results in *caput membranaceum* with shortened and deformed limbs noted. Some affected neonates survive for several days or weeks. The neonates often succumb to respiratory failure brought on by pulmonary hypoplasia and structural failure of the weakened skeleton from demineralization.

Prenatal therapy for inborn errors of metabolism remains an unmet challenge. Most cases of perinatal HPP with severe skeletal hypomineralization result in stillbirth or postnatal lethality. Over 50% of the patients with an infantile form of the condition die within the next few months. Advanced ultrasonography made in utero diagnosis of severe skeletal dysplasia including HPP feasible.

Acidic amino acid (AAA) oligopeptides bind specifically to bone matrix, hydroxyapatite calcium site, and tagging a therapeutic agent, namely TNSALP, with AAA markedly enhances delivery of the agent to bone [Nishioka et al., (2006) Mol Genet Metab, 88 (3):244-255]. ERT has been successively shown by a deca-Asp ($D_{10}$)-tagged TNSALP (sALP-$FcD_{10}$) in a HPP murine model (similar to the infantile form in human patients) to lead to marked clinical and pathological improvement [Milian et al., (2008) J Bone Miner Res, 23 (6):777-787]. The sALP-$FcD_{10}$ enzyme is now used in Phase I and II clinical trials for HPP patients, resulting in substantial reversal of bone hypomineralization [Whyte et al., Hypophosphatasia: Treatment of Life-Threatening Disease Using Bone-Targeted Human Recombinant Tissue Non-Specific Alkaline Phosphatase (2009) ACR/ARHP Scientific Meeting, found at acr.confex.com/acr/2009/webprogram/Paper12463.html. This sALP-$FcD_{10}$ enzyme also includes the Fc region of human IgG at the C-terminus of the enzyme for purification purposes.

Recently, Grubb et al. showed that Fc-conjugated β-glucuronidase, infused into pregnant mice, was transported across the placenta, indicating a potential application for prenatal therapy [Grubb et al., (2008) *Proc Natl Acad Sci U.S.A.*, 105(24):8375-8380]. β-glucuronidase (GUS) is a cytosol- and water-soluble, sialic acid-containing glycoprotein enzyme that catalyzes breakdown of complex carbohydrates. Maternal IgG is transported transplacentally by the neonatal Fc receptor, which recognizes the Fc domain of IgG and mediates transcytosis from maternal to fetal circulation.

SUMMARY OF THE INVENTION

The inventors have made the surprising discovery that polypeptides that are linked to an immunoglobulin fraction-crystallizable domain (Fc-domain) are able to cross the placenta and to enter the circulation of the fetus. Thus, one aspect of the invention contemplates a fusion protein comprised of a polypeptide peptide-bonded to a Fc-domain. A preferred polypeptide has a therapeutic use, such as a metabolic enzyme. A more preferred polypeptide is a cytosol-soluble (water-soluble) portion of a membrane-bound enzyme. A most preferred polypeptide is a tissue-nonspecific alkaline phosphatase (TNSALP).

Another aspect of the invention contemplates a pharmaceutical composition that comprises an effective amount of an above-described fusion protein dissolved or dispersed in a pharmaceutically acceptable carrier. Such a carrier is typically an isotonic aqueous buffer.

Yet another aspect of the invention contemplates transplacental enzyme replacement therapy (ERT) for deficiency of a polypeptide such a TNSALP by administering a before-described pharmaceutical composition to a pregnant animal whose fetus or embryo is in need of such therapy. An exemplary fusion protein of such a composition comprises a water-soluble TNSALP portion, e.g., C-terminus-truncated TNSALP peptide-bonded to an IgG1 antibody Fc portion.

Administration may be by any route, preferably intravenous or intraperitoneal administration of the fusion protein. Inborn errors of metabolism comprise diseases, which include MPS (such as MPS VII) and hyphosphatasia. The fusion protein (also some times referred to herein as a chimeric polypeptide) has a therapeutic domain and a Fc-domain as described herein.

BRIEF DESCRIPTION OF THE DRAWINGS

In the accompanying drawings, which form a part of the specification and are to be read in conjunction therewith.

DETAILED DESCRIPTION OF THE INVENTION

Applicants discovered that the prenatal delivery of a fusion protein containing the IgG Fc-domain, which after infusion into the maternal circulation, mediates delivery of the fusion protein across the placenta into the circulation of the fetus or embryo. An embryo is often described in the human context as existing from conception to about the eighth week, whereas a fetus is often described as being from about nine weeks to birth. Specifically, the present invention contemplates a fusion protein having an IgG1 Fc peptide portion peptide bonded to a water-soluble (cytosol-soluble) portion of a biologically active polypeptide that is normally membrane-bound such as tissue-nonspecific alkaline phosphatase (TNSALP) or HMG-CoA reductase. The present invention also contemplates a composition containing an effective amount of the fusion protein dissolved or dispersed in a pharmaceutically acceptable carrier. A method of treating a deficiency of that biologically active polypeptide in a fetus or embryo contemplates administering the pharmaceutical composition to the pregnant animal such as a mouse or a human whose fetus or embryo is in need of the biologically active polypeptide so that the fusion protein crosses the placenta.

A contemplated fusion protein is dissolved, dispersed or admixed in a composition that is pharmaceutically acceptable and compatible with the active ingredient as is well known. The phrases "pharmaceutically acceptable" or "physiologically tolerable" refer to molecular entities and compositions that typically do not produce an allergic or similar untoward reaction, and the like, when administered to a host mammal.

Suitable carriers can take a wide variety of forms depending on the intended use and are, for example, aqueous solutions containing saline, phosphate buffered saline (PBS), dextrose, glycerol, ethanol, or the like and combinations thereof. In addition, if desired, a composition can contain minor amounts of auxiliary substances such as wetting or emulsifying agents, pH buffering agents, mineral oils, which enhance the effectiveness of the composition. A preferred embodiment contains at least about 0.01 percent to about 99 percent of an isolated fusion polypeptide of this invention as an active ingredient, typically at a concentration of about 10 to 200 mg of fusion protein per milliliter (ml) of carrier.

A contemplated composition is conventionally administered parenterally as an aqueous composition, by injection, for example, intraperitoneally, subcutaneously or intramuscularly. The administration is provided to a pregnant human patient or suitable animal host such as a chimpanzee, mouse, rat, horse, sheep, mouse, dog, goat, bovine, monkey, or the like whose fetus or embryo is in need of the biologically active polypeptide. A contemplated composition is thus typically provided as a unit dosage amount in dry form that can be readied for administration by addition and mixing of deionized or distilled or other sterile water.

The amount of fusion protein utilized in each administration is referred to as an effective amount and can vary widely, depending inter alia, upon the fusion protein, the genus of the animal to which the a fusion protein is administered, and the severity of the disease state being treated. An effective amount of a fusion protein at least temporarily improves the disease state for which the fusion protein is administered. In the illustrative example used herein, heterozygous pregnant mice were infused with 10 U/g body weight of TNSALP-hFc on embryonic days 17.5 and that administration was successful in raising the level of TNSALP circulating in the fetal mice to almost twice the amount of enzyme present in untreated mice. The amount selected as an effective amount of a fusion protein can be determined for a given animal host and disease by a skilled worker without undue experimentation.

It is advantageous to treat severely affected fetuses or embryos with enzyme replacement therapies (ERTs) before birth to minimize the deficiency in utero such as bone hypomineralization. The disclosure provided hereinafter illustrate that the present invention can be applied to the prenatal treatment of hypophosphatasia (HPP) as an illustrative fetal or embryonic disease that can be so treated.

Figure 1:
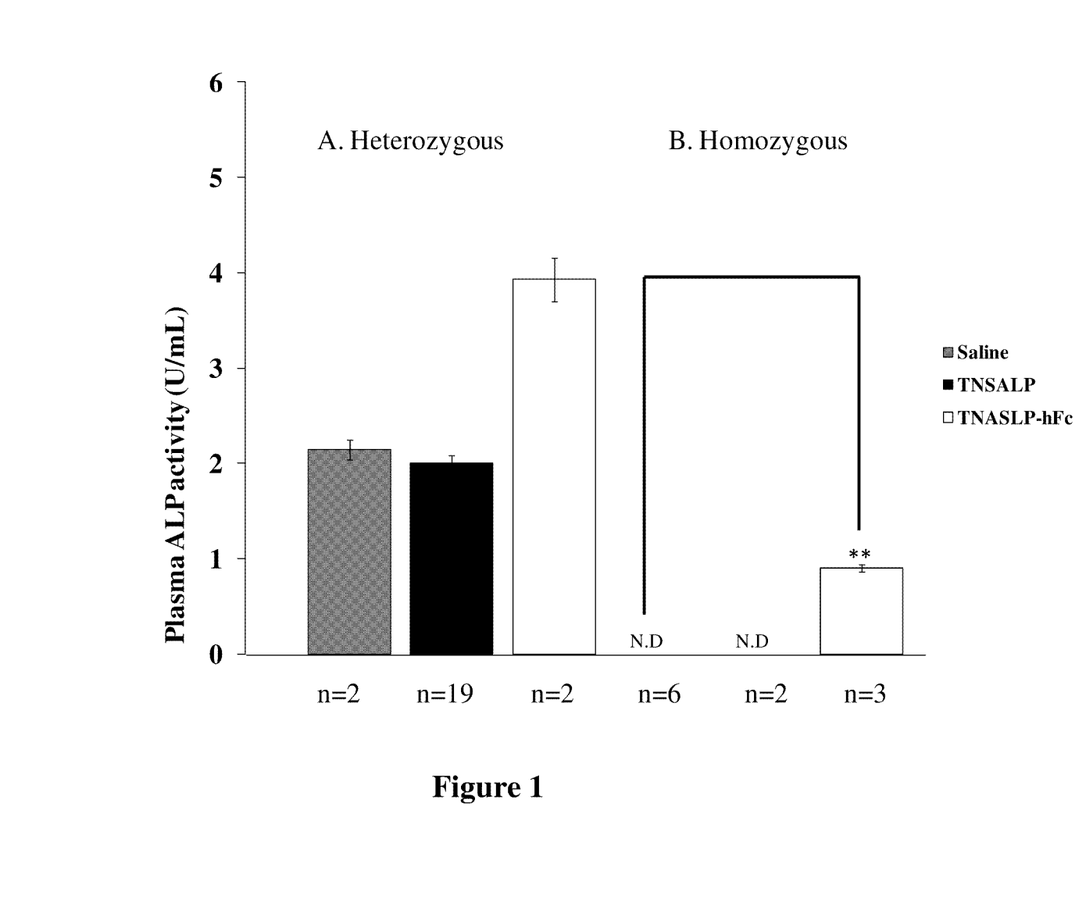
FIG. 1 is a graphic representation of the results of transplacental transfer of TNSALP-Fc after intravenous infusion into pregnant mice.
Figure 2:
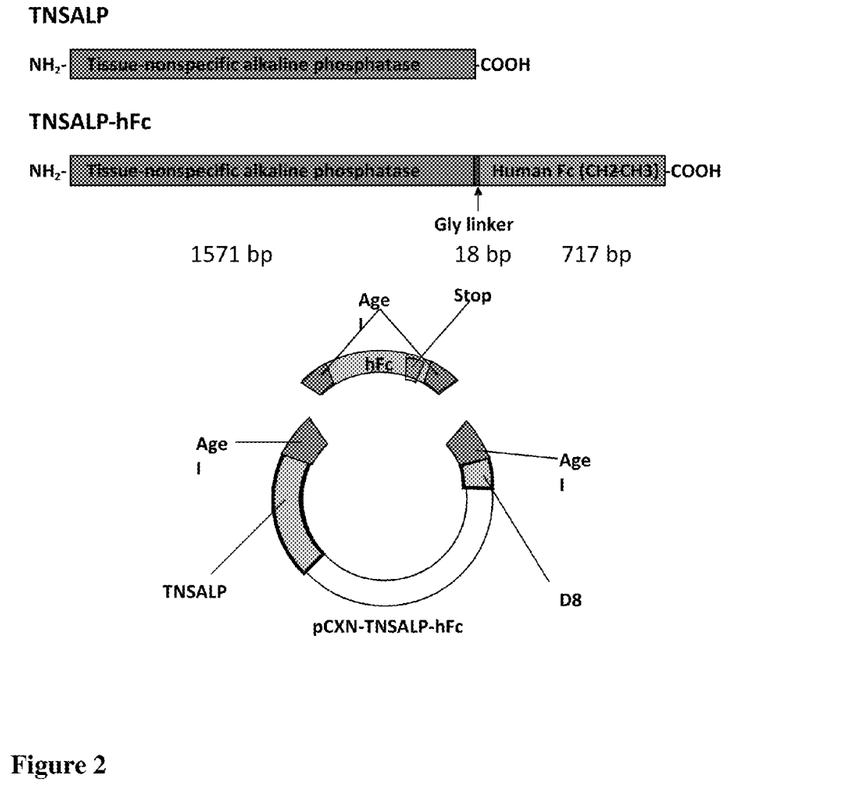
FIG. 2 is a schematic drawing showing TNSALP-hFc constructions in mammalian expression vector pCXN.

The transplacental approach can be used for the prenatal treatment of HPP, which will have a significant impact on clinical practice. To illustrate that the present invention can be applied to the prenatal treatment of HPP in a murine model, a fusion protein comprising the C-terminal, hydrophobic, membrane-spanning portion of TNSALP was expressed as a fusion protein with the IgG1 $CH_2$—$CH_3$ hFc portion (TNSALP-hFc). That fusion protein was compared with the untagged recombinant TNSALP for clearance from the maternal circulation and delivery to the fetus. To determine whether TNSALP-hFc could be transferred across the placenta, ALP activity in plasma of HPP newborns born from HPP heterozygous females mated with HPP heterozygous males was examined. It was observed that TNSALP-hFc, infused into pregnant mice on embryonic day 17.5, was transported across the placenta, whereas untagged TNSALP was not delivered to the fetus. These results are shown in FIG. 1.

These results can be translated into transplacental ERT because the hFc-conjugated TNSALP is already clinically investigated for ERT in HPP patients. To produce the results shown in FIG. 1, heterozygous male and female mice were mated to produce HPP offspring. Heterozygous pregnant mice were infused with 10 U/g body weight of TNSALP-hFc, untagged TNSALP, or saline on embryonic days 17.5. The pups were tested and the following was found:

A) The heterozygous pups produced by the pregnant mice treated with TNSALP-hFc increased plasma activity (3.930±0.228 U/mL n=2); however, the heterozygous pups produced by saline or untagged TNSALP infused pregnant mice had the same levels of 2.143±0.101 U/mL (n=2) and 2.009±0.075 U/mL (n=19), respectively.

B) A similar increase was observed in homozygous pups produced by treated pregnant mice. Plasma ALP levels of 1-day-old homozygous pups derived from pregnant mice treated with untagged TNSALP were not detectable (N.D.), whereas the pregnant mice, which were infused with TNSALP-hFc, produced homozygous pups that contained 50% of normal levels of plasma ALP activity (0.904±0.036 U/mL, n=3).

Thus, in one embodiment of the present invention, the C-terminus-anchorless TNSALP enzyme was produced and the secreted form tagged with $CH_2$—$CH_3$ hFc portion to form a fusion protein that was expressed using Chinese Hamster Ovarian (CHO) cell line and showed transplacental activity in fetus on hypophosphatasia mice with ERT. The present invention indicated that the enzyme with IgG1 $CH_2$—$CH_3$ hFc portion is effective as a therapeutic agent transplacentally. This method is applicable to other proteins whose deficiency leads to the other human disorders with deficiency of an enzyme such as fetal hypolipidemia using the C-terminal membrane anchor truncated HMG-CoA reductase. See, U.S. Pat. No. 5,460,949 for a useful sequence.

Here, first, the TNSALP and TNSALP-hFc were purified by the following two-step column procedure. Tris buffer was 25 mM Tris-HCl, pH 8.0, containing 0.1 mM magnesium chloride and 0.01 mM zinc chloride. Unless stated otherwise, all steps were performed at 4° C. The following procedure was followed:

Step 1. The medium-containing enzyme was filtered through a 0.2 μm filter and then dialyzed against Tris buffer using Amicon stirred-cell ultrafiltration unit with Millipore ultrafiltration membrane YM-30.

Step 2. The dialyzed medium was applied to a column of DEAE-Sepharose equilibrated with Tris buffer. The column was first washed with Tris buffer and then the enzyme was eluted with 0 to 0.4 M NaCl in a linear gradient.

Step 3. The active eluted fractions were pooled and dialyzed against Tris buffer containing 0.1 M NaCl by using Centricon centrifugal filter device with Millipore ultrafiltration YM-10 filter. The dialyzed fractions were then concentrated for Step 4.

Step 4. The concentrated enzyme was applied to a column of Sephacryl S-400-HR equilibrated with Tris buffer containing 0.1 M NaCl. The enzyme was eluted with Tris buffer containing 0.1 M NaCl.

Step 5. The active eluted fractions were pooled and dialyzed against Tris buffer containing 0.1 M NaCl by using Centricon centrifugal filter device with Millipore ultrafiltration YM-10 filter. The dialyzed fractions were then concentrated and stored at −80° C. until use.

Figure 3:
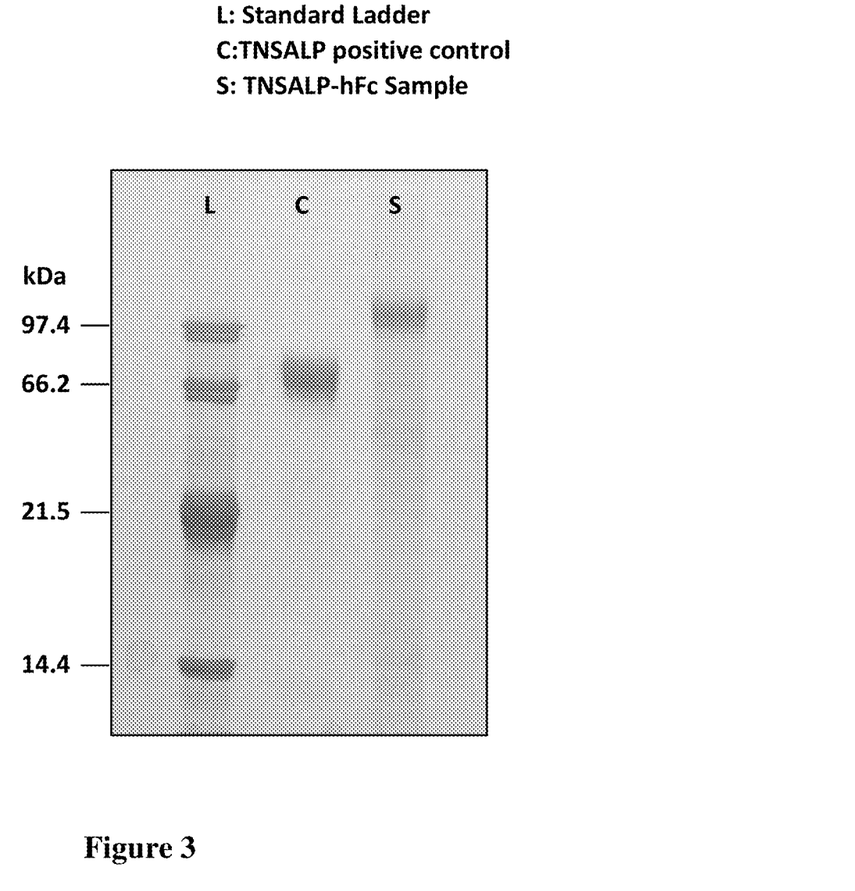
FIG. 3 is a schematic drawing showing a top view of SDS-PAGE results for purified TNSALP and TNSALP-hFc.

To characterize the purified TNSALP-hFc, a polyacrylamide gel electrophoresis in the presence of sodium dodecyl sulfate (SDS-PAGE) was performed, followed by silver staining. This is shown in FIG. 3.

The TNSALP and TNSALP-hFc activity were measured using the 250 μl of 10 mM p-nitrophenyl phosphate (pNPP) as substrate in 1 M diethanolamine, pH 9.8, containing 1 mM magnesium chloride, 0.02 mM zinc chloride, and incubated at 37° C. The time-dependent increase in absorbance at 405 nm (reflecting p-nitrophenolate production) was measured on a plate spectrophotometer. One unit of activity was defined as the quantity of enzyme that catalyzed the hydrolysis of 1 μmol substrate in 1 minute.

Figure 4:
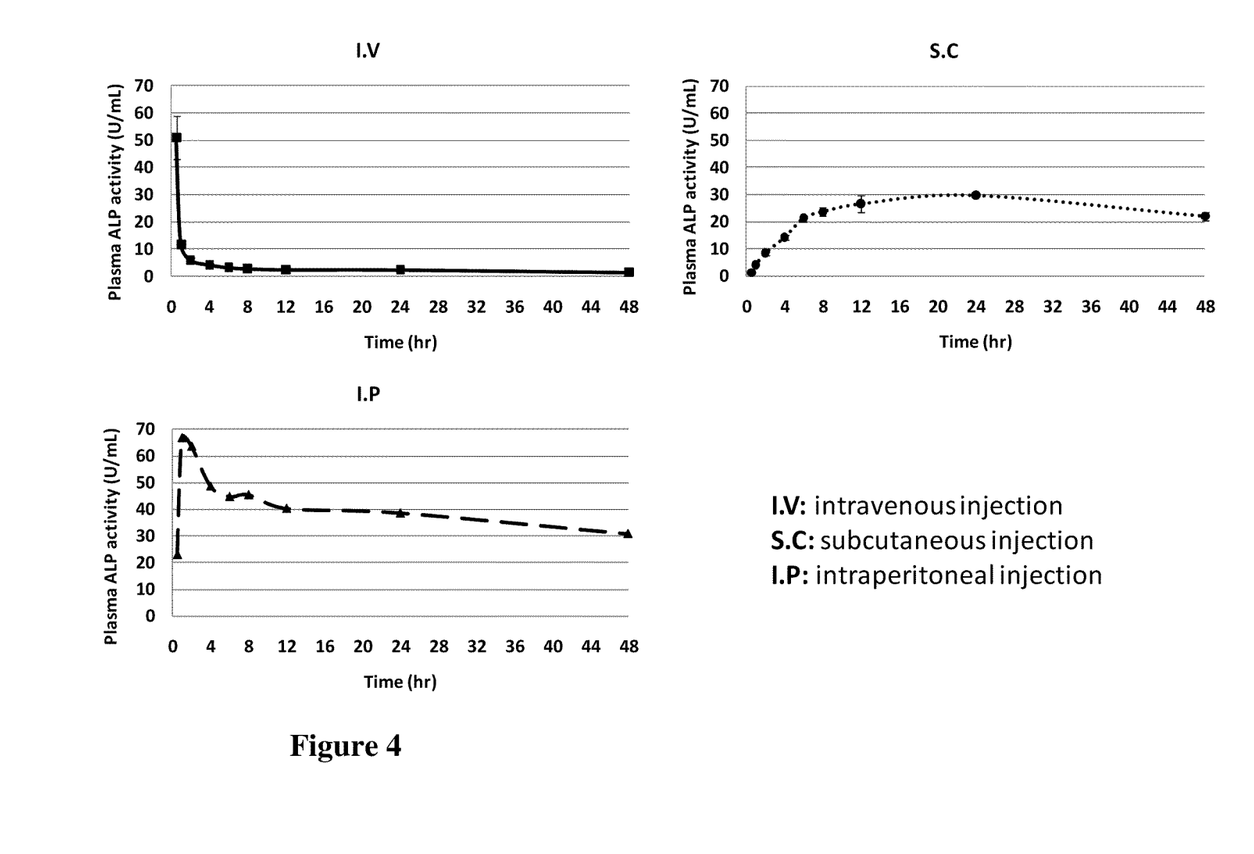
FIG. 4 is a series of graphs showing the pharmacokinetics of different administration of infusions by using TNSALP-hFc.

Table 1 below provides the data analyses of the pharmacokinetics. One month-old wild type mice were infused with TNSALP-hFc enzyme by intravenously (i.v), subcutaneously (s.c), and intraperitoneally (i.p) methods, and those administration dose concentration was fixed by 10 U/g body weight (FIG. 4). After infusion, the blood samples were collected to measure the level of TNSALP-hFc activity respective time course (0-48 hours). The peak concentration (Cmax) and concentration peak time (Tmax) were measured by original data. The area under the curve (AUC) was obtained with use of the lin-lin trapezoidal rule. The terminal elimination rate constant (ke) was calculated by log-linear regression of the final data points. The apparent elimination half-life time (T½) was calculated as follows: 0.693/ke. The mean residence time (MRT) was calculated to divide the area under the first moment curve by the AUC. The total clearance (CL) was calculated to divide the dose concentration by the AUC. The steady-state distribution volume (Vd) was calculated to divide the CL by the MRT. The bioavailability was calculated to divide the AUC of each administration method by the AUC of intravenous method. Those parameters were followed by actual TNSALP-hFc activity of each time point. The data for the parameters are found in Table 1 hereinbelow and are represented graphically in FIG. 4.

TABLE 1

| Pharmacokinetics Parameter Mice Age 1 month-old Enzyme TNSALP-hFc | | | |
|---|---|---|---|
| injection manner | i.v | s.c | i.p |
| Dose (U/g) | 10 | 10 | 10 |
| T½ (hr) | 29.9 | 54.1 | 33.9 |
| Tmax (hr) | 0.5 | 24 | 1 |
| Cmax (U/mL) | 50.9 | 29.8 | 67 |
| AUC (U/mL * hr) | 139.4 | 1172.3 | 1866.9 |
| Bioavailability (%) | 100 | 840.7 | 1338.9 |
| MRT (mean residence time) (hr) | 11.8 | 16.7 | 14.5 |
| Vd (mL/g) | 0.848 | 0.143 | 0.078 |
| CL (mL/(hr * g)) | 0.0717 | 0.0085 | 0.0054 |

As provided herein, the nucleotide base sequence is found in SEQ ID NO:1 and the derived amino acid residue sequence is provided in SEQ ID NO:2. Another aspect of the invention provides a composition comprising a nucleotide sequence as set forth in SEQ ID NO:1. Another aspect of the invention provides a composition comprising a polypeptide as set forth in SEQ IS NO:2.

The invention provides for a method for treating a metabolic disorder, such as HPP, in a fetus or embryo were a protein having a sequence as set forth in SEQ ID NO:2 is administered to a pregnant mother. The fusion protein comprises a Fc fragment of IgG1 and a soluable TNSALP. The protein crosses the placenta of the mother and enters the fetal blood stream. The protein is taken up into fetal tissue such that the TNSALP restores normal metabolic activity in the fetus.

An isolated polypeptide of this invention can be formulated into a composition as a neutral or salt form. Pharmaceutically acceptable salts, include the acid addition salts (formed with the free amino groups of the protein or antigen) and which are formed with inorganic acids such as, for example, hydrochloric or phosphoric acids, or such organic acids as acetic, oxalic, tartaric, mandelic, and the like. Salts formed with the free carboxyl groups can also be prepared from inorganic bases such as, for example, sodium, potassium, ammonium, calcium, or ferric hydroxides, and such organic bases as isopropylamine, trimethylamine, histidine, procaine, and the like.

A composition of this invention can be administered in a manner compatible with the formulation for the composition, and in such an amount as is effective to induce an antibody-producing immune response. The quantity of composition to be administered to achieve a desired result depends on the judgment of the practitioner and is peculiar to each individual host mammal, but are well known for laboratory hosts such as mice, rats, rabbits, goats and the like.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Because many possible embodiments can be made of the invention without departing from the scope thereof, it is to be understood that all matter herein set forth is to be interpreted as illustrative, and not in a limiting sense.

What is claimed is:

1. A method for treating hypophosphatasia in a fetus or embryo comprising the step of parenterally delivering a fusion protein having the sequence as set forth in SEQ ID NO:2 to a pregnant mother, wherein said fusion protein comprises a Fc fragment of an IgG antibody and a tissue-nonspecific alkaline phosphatase enzyme, and wherein said fusion protein crosses a placenta of said mother and enters said fetus's or embryo's blood stream, and wherein said fusion protein is taken up into fetal or embryonic tissue such that said enzyme restores normal mineralization activity in said fetus or embryo.

2. The method of claim 1, wherein said fusion protein is delivered intraperitoneally or subcutaneously.

* * * * *